US010968164B2

(12) United States Patent
Raaijmakers et al.

(10) Patent No.: US 10,968,164 B2
(45) Date of Patent: Apr. 6, 2021

(54) PROCESS TO CONVERT THE CYCLIC MONOUREA OF AN ETHYLENE AMINE COMPOUND INTO THE ETHYLENE AMINE COMPOUND

(71) Applicant: NOURYON CHEMICALS INTERNATIONAL B.V., Arnhem (NL)

(72) Inventors: Michiel Jozef Thomas Raaijmakers, Deventer (NL); Antoon Jacob Berend Ten Kate, Arnhem (NL); Eike Nicolas Kantzer, Uddevalla (SE); Rens Veneman, Amersfoort (NL); Slavisa Jovic, Utrecht (NL); Rolf Krister Edvinsson, Partille (SE); Karl Fredrik Lake, Södertälje (SE); Hendrik Van Dam, Ede (NL); Ina Ehlers, Stenungsund (SE); Sara Erika Tönnerfors, Södertälje (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/638,345

(22) PCT Filed: Aug. 7, 2018

(86) PCT No.: PCT/EP2018/071316
§ 371 (c)(1),
(2) Date: Feb. 11, 2020

(87) PCT Pub. No.: WO2019/030188
PCT Pub. Date: Feb. 14, 2019

(65) Prior Publication Data
US 2020/0223785 A1 Jul. 16, 2020

(30) Foreign Application Priority Data
Aug. 11, 2017 (EP) .................................... 17185940

(51) Int. Cl.
*C07C 209/62* (2006.01)
*C07C 209/86* (2006.01)
(52) U.S. Cl.
CPC .......... *C07C 209/62* (2013.01); *C07C 209/86* (2013.01)
(58) Field of Classification Search
CPC ........................ C07C 209/62; C07C 209/86
See application file for complete search history.

(56) References Cited

U.S. PATENT DOCUMENTS

| 2,812,333 | A | | 11/1957 | Steele | |
|---|---|---|---|---|---|
| 4,650,906 | A | * | 3/1987 | Murakami | C07C 209/86 544/358 |
| 5,491,263 | A | * | 2/1996 | Rooney | C07C 209/16 544/401 |
| 10,428,010 | B2 | * | 10/2019 | Edvinsson | C07D 233/36 |
| 2009/0065346 | A1 | * | 3/2009 | Pickenacker | C07C 211/14 203/32 |
| 2011/0015439 | A1 | * | 1/2011 | Hanson | C07C 209/16 564/475 |
| 2019/0031597 | A1 | * | 1/2019 | Edvinsson | C07C 209/62 |
| 2019/0039993 | A1 | * | 2/2019 | Edvinsson | C07C 269/06 |
| 2019/0039994 | A1 | * | 2/2019 | Edvinsson | C07C 209/62 |
| 2019/0308930 | A1 | * | 10/2019 | Kantzer | C07C 209/62 |
| 2020/0071260 | A1 | * | 3/2020 | Kantzer | C07C 213/02 |
| 2020/0165187 | A1 | * | 5/2020 | Ten Kate | C07C 209/62 |
| 2020/0165212 | A1 | * | 5/2020 | Raaijmakers | C07D 233/34 |
| 2020/0199060 | A1 | * | 6/2020 | Ten Kate | C07C 209/62 |
| 2020/0207701 | A1 | * | 7/2020 | Veneman | C07C 209/16 |
| 2020/0223800 | A1 | * | 7/2020 | Ten Kate | C07D 233/34 |

FOREIGN PATENT DOCUMENTS

| WO | WO-2017137529 A1 | * | 8/2017 | ........... C07C 209/62 |
|---|---|---|---|---|
| WO | WO-2019011709 A1 | * | 1/2019 | ........... C07C 209/16 |
| WO | WO-2019030189 A1 | * | 2/2019 | ........... C07C 211/14 |
| WO | WO-2019030193 A1 | * | 2/2019 | ........... C07C 213/02 |

OTHER PUBLICATIONS

G. Vasanthakumar et al., 37 Synthetic Communications (2007) (Year: 2007).*
EPO, European Extended Search Report issued in European Application No. 17185940.8, dated Jan. 11, 2018.
EPO, International Search Report and Written Opinion issued in International Application No. PCT/EP2018/071316, dated Oct. 16, 2018.
Vasanthakumar, G.R. et al., "Hydrolysis of Cyclic Ureas under Microwave Irradiation: Syntheses and characterization of 7,8-Diaminopelargonic Acid", Aug. 1, 2007, pp. 2633-2639, vol. 37, No. 16.

* cited by examiner

*Primary Examiner* — Alexander R Pagano
(74) *Attorney, Agent, or Firm* — Lorenz & Kopf, LLP

(57) ABSTRACT

A process to convert the cyclic monourea of ethylene amine compounds (U-EA) into ethylene amine compound (EA) is provided. The process may include performing a reactive separation step using a reaction mixture containing the cyclic monourea, wherein one cyclic monourea (U-EA) reacts with another cyclic monourea (U-EA) to transfer its urea unit thereto. The process may further include separating the obtained ethylene amine compound (EA) without urea unit from the reaction mixture.

9 Claims, No Drawings

PROCESS TO CONVERT THE CYCLIC MONOUREA OF AN ETHYLENE AMINE COMPOUND INTO THE ETHYLENE AMINE COMPOUND

CROSS-REFERENCE TO RELATED APPLICATION

This application is a U.S. National-Stage entry under 35 U.S.C. § 371 based on International Application No. PCT/EP2018/071316, filed Aug. 7, 2018, which was published under PCT Article 21(2) and which claims priority to European Application No. 17185940.8, filed Aug. 11, 2017, which are all hereby incorporated in their entirety by reference.

TECHNICAL FIELD

The present invention relates to a process to convert a cyclic monourea of an ethylene amine compound into the corresponding ethyleneamine compound by a reactive separation process.

BACKGROUND

Two adjacent nitrogen atoms linked by one alkylene unit and one carbonyl moiety form a cyclic alkylene urea. When alkylene is ethylene, an ethylene amine (EA) in which two nitrogen atoms are linked intramolecular by a carbonyl moiety

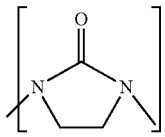

is here referred to as an UEA. Replacing the carbonyl bridge with two hydrogen atoms yields the corresponding ethylene amine. For example: EU↔EDA, UDETA↔DETA, UAEEA↔AEEA, UTETA↔L-TETA, UTEPA↔L-TEPA. Some higher amines host more than one carbonyl moiety, e.g. DUTETA the diurea of L-TETA. The carbonyl moiety may link nitrogen atoms on two separate molecules. For example H2NC2H4NH—CO—NHC2H4NH2 and replacing the carbonyl moiety with two hydrogen atoms here yields two EDA. As to naming of the molecules, EDA stands for ethylenediamine, DETA for diethylenetriamine, L-TETA for linear triethylenetetraamine, L-TEPA for linear tetraethylenepentamine, L-PEHA for linear pentaethylenehexamine, AEEA stands for aminoethylethanolamine. When there is a single cyclic urea in the molecule this is indicated by adding a U in front of the name, e.g. UTETA means the cyclic urea of L-TETA, while when there are two cyclic ureas in the molecule this is indicated by DU, i.e. DUTETA means the internal cyclic diurea of L-TETA. If there is a number indicated for the U this refers to the amino group where the U group is located. U1TETA is the monocyclic urea of L-TETA wherein the urea is between the first (terminal) and the second amine unit, U2-TETA is the monocyclic urea of L-TETA wherein the urea is between the second and third amine group in the TETA molecule (i.e. an internal cyclic urea is formed). DUTETA or DU1,3TETA is the dicyclic urea of L-TETA, the cyclic urea units inherently being between the first and second amine group, and the third and fourth amine group, respectively. DUTEPA exists in two versions DU1,3-TEPA and DU1,4-TEPA. There is one exception to this naming and that is that instead of UEDA the abbreviation EU is used, which stands for ethyleneurea. It is possible that between two amine groups in an alkylene amine two alkylene groups are present, resulting in a so-called cyclic unit (when having two ethylenes this cyclic unit is called a piperazine unit). This is indicated by adding a C in front of the name, e.g. CTETA means L-TETA wherein one unit —HN—C2H4-NH— is present as

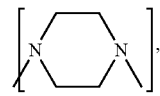

If there is a number indicated with the C this refers to the amino group where the cyclic group is located. As an example N-[(2-aminoethyl)2-aminoethyl]piperazine is in this document referred to as C1-TETA.

Pending application PCT/EP2017/052944 relates to a process to convert cyclic alkylene ureas into their corresponding alkylene amines wherein the process is performed by reaction with an amine compound and wherein the amine compound is a primary amine, a cyclic secondary amine or a bicyclic tertiary amine.

Though it was already unexpectedly found that amines, which are much weaker bases than the inorganic caustic bases disclosed earlier, are effective in converting cyclic alkylene ureas into their corresponding (linear) alkylene amines at good yields it has now been even found possible to remove a urea unit from an ethylene amine compound in a reactive separation process in which one cyclic urea-containing ethylene amine reacts with another one and accepts the urea unit therefrom while simultaneously removing the urea-free ethylene amine compound.

BRIEF SUMMARY

A process to convert the cyclic monourea of ethylene amine compounds (U-EA) into ethylene amine compound (EA) is provided. An exemplary process includes performing a reactive separation step using a reaction mixture containing the cyclic monourea, wherein one cyclic monourea (U-EA) reacts with another cyclic monourea (U-EA) to transfer its urea unit thereto. Further, the exemplary process includes separating the obtained ethylene amine compound (EA) from the reaction mixture.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

The present invention now provides a process to convert the cyclic monourea of ethylene amine compounds (U-EA) into ethylene amine compound (EA) by performing a reactive separation step using a reaction mixture containing the cyclic monourea, wherein one cyclic monourea (U-EA) reacts with another cyclic monourea (U-EA) to transfer its urea unit thereto and the obtained ethylene amine compound (EA) without urea unit is separated from the reaction mixture.

A reaction wherein all or at least a substantial part of the urea groups end up on part of the molecules and that at the same time creates also urea-free molecules can only run if the conditions are such that after the transfer of the urea from one molecule to another molecule the urea-free molecule is removed from the reaction mixture because if such were not the case the reaction mixture would settle again with a more or less even distribution of all urea units over the available molecules. The present invention hence resides in acknowledging that such conditions are available when taking the cyclic monourea of an ethylene amine such as TETA or TEPA as a feedstock for the reactive separation process, and establishing that the boiling point of any U-EA, such as UTETA or UTEPA, is higher than that of the corresponding EA, such as TETA or TEPA respectively, and that urea transfer between molecules finds place under conditions at which part of the reaction mixture is transferred to the vapor phase, in embodiments corresponding with conditions that are very close to the boiling points of the molecules.

The process of the present invention can be represented by below reaction formula: 2 U-EA→EA↑+DU-EA (wherein the up-arrow indicates that the EA is separated from the reaction mixture)

In a preferred embodiment the ethyleneamine compound EA is triethylenetetraamine (TETA) and/or tetraethylene pentamine (TEPA), most preferred it is TETA and the reaction mixture, hence, preferably contains a cyclic monourea of respectively TETA and/or TEPA, most preferred a cyclic monourea of TETA.

In an embodiment the TETA or TEPA can be partly present as an analogue such as UPEEDA, and the reaction then partially finds place as for example UPEEDA+ UTETA=>PEEDA+DUTETA, wherein PEEDA stands for N-[(2-aminoethyl)2-aminoethyl]piperazine.

Unexpectedly, when using the process of the present invention alkylene amine product is with high efficiency formed and simultaneously separated from the reaction mixture in a good yield using relatively mild conditions. The urea free compounds can be prepared and isolated as one fraction at relatively low temperatures, especially urea free compounds that are relatively volatile. Because cyclic alkylene ureas are used to convert cyclic alkylene ureas into their corresponding alkylene amines, degradation of the alkylene amines is to a large extent avoided, like might occur during treatment with strong bases like NaOH or strong acids like HCl. The process of the present invention has as a further advantage that water or any other adjuvant need not be added and that the respectively obtained alkylene diurea can be also recovered as products.

Examples of reactive separation processes are process driven by volatility differences such as for example reactive flashing, membrane distillation, membrane evaporation, stripping or reactive distillation, whereby reactive distillation is preferred.

In a preferred embodiment of the process the reaction mixture contains less than 10 wt %, more preferred less than 7 wt %, even more preferred less than 5 wt % of water on the basis of total weight of the reaction mixture. In certain embodiments, numbers in this description indicating amounts, ratios of materials, physical properties of materials, and/or use are may be understood as being modified by the word "about". The term "about" as used in connection with a numerical value and the claims denotes an interval of accuracy, familiar and acceptable to a person skilled in the art. In general, such interval of accuracy is ±10%.

In another preferred embodiment wherein more than the required amount of water is present in a composition of cyclic alkylene ureas and optionally the amine compound, it is preferred to first perform a step wherein excess of water is removed. Such a step may involve a water evaporation, flashing, stripping, extraction, adsorption or other physical step as well as chemical water scavenging techniques known to the person skilled in the art, preferably by a distillation step.

The reaction can be done under any conditions enabling the transfer of the urea unit and vaporizing the urea free "empty" ethylene amine involved. The process of the invention is preferably done at a temperature of at least 150° C., preferably at least 200° C., more preferably at least 230° C., and most preferably of at least 250° C. Preferably the temperature during the process does not exceed 400° C., more preferably 350° C.

Pressure requirement depends on operating temperature and composition. Operation should preferably be below 1 bara. More preferably, the distillation is performed below 100 mbara. Even more preferably below 10 mbara.

In another preferred embodiment the reaction is done at a pressure of at least 0.1 mbar.

A person skilled in the art will be capable of optimizing the conditions, i.e. temperature, pressure and auxiliary compounds such as stripping gases, dependent on the ethylene amines to be separated.

The process of the present invention is in embodiments is performed for a time of between 1 minute and 12 hours. Preferably the reactive separation is run in less than 10 hours, more preferably in less than 8 hours, most preferably less than 5 hours.

The process of the invention may contain a subsequent step wherein any urea compound DU-EA formed, or more in general the remaining (heavy) fraction of the reactive separation process containing the DU-EA compounds, is hydrolyzed with water, optionally containing a base or an acid, to release one or more of its carbonyl groups which can then be recycled into the process or separated off, for example as carbon dioxide or a ionic derivative thereof (such as hydrogen carbonate or carbonate salt). It should be noted that in embodiments of the present invention the cyclic urea unit of the newly formed urea compound is easier removed with a hydrolysis step than the urea of the starting cyclic urea compound. Also the newly formed cyclic urea compounds are in embodiments less susceptible to degradation during such hydrolysis than the starting cyclic urea compounds. Both these phenomena make the process of the present invention very favorable for such embodiments.

In a further preferred embodiment the released carbonyl group, i.e. often carbon dioxide, is continuously removed from the process which will enhance the process. The carbon dioxide can be removed for example by working in a suitable reactor unit comprising or connected to a section for actively removing CO2 by desorption, for instance by distillation, stripping or flashing, with or without a membrane.

In preferred embodiments the above subsequent step of hydrolyzing a formed diurea to releasing carbon dioxide is performed by at least a step in which the materials are stripped. A person skilled in the art will know that such a stripping step is suitably done by having a sufficiently high flow of carrier gas and by ensuring good mixing and proper gas to liquid contact so that the maximum amount of carbon dioxide is removed from the system, in any way, the carbon dioxide should be so removed or isolated that it will not recombine with the urea compound, or any other amine compound.

In another preferred embodiment of the invention the amine compound or any urea compound formed from the reaction between the amine compound and the cyclic urea compound are recycled back into the process or separated off.

While performing the process of the present invention further compounds can be present in the reaction mixture, such compounds include in embodiments further ethylene amines and ethanol amines. More preferably if any further ethylene amines and ethanol amines are present these are of a higher molecular weight than the TETA or TEPA that is prepared.

Examples of further compounds that can be present during the process of the invention include U2TETA, DETA, UDETA, HEDETA, HETETA, UHETETA, DUHETETA, TEPA, UTEPA, DUTEPA, PEHA, DUPEHA, TUPEHA, C1, C2 and C3 analogues (which means as indicated above that one of the ethylene units is present as a diethylene unit/piperazine unit, the number indicating the amine where this piperazine unit is located counting from the terminal amine) of the above mentioned components, or C1 and C2 analogues of TETA such as N-[(2-aminoethyl)2-aminoethyl] piperazine or N,N'-bis-(2-aminoethyl)piperazine), or AEEA and its urea and carbamate counterparts, or linear ureas such as diethyleneurea, AEEAUAEEA, EDAUAEEA, EDAUTETA, TETAUTETA, and other linear urea analogues of combinations of the above components.

The process can be carried out in a batch reactor, possibly fed-batch operation, or in a continuously operating system such as in a cascade of continuous flow reactor.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

In such a scheme, the cyclic alkylene urea, and possibly adjuvants such as water, may be fed to the equipment as desired at a single point or at multiple points throughout the process equipment, which may include continuously stirred tank reactors, tubes, pipes, reactive distillation columns, reactive stripping units or combinations thereof.

In embodiments wherein a reactive distillation apparatus is used, the apparatus may comprise a reactive distillation column comprising at least one column internal, which column is on one side connected to a cooler unit and on the other side connected to a reboiler, and which apparatus is provided with an inlet for supplying the amine mixture, and one or more outlets for different distillate fractions. The process can be operated in batch-mode, fed-batch mode, or continuously.

The process of the present invention typically depends on a number of reaction parameters such as the pressure in the column, the exact composition to be separated, like the presence/absence of relatively volatile components, such as stripping gases, and less volatile components, the mass ratio of $H_2O$ to cyclic urea, the number and/or type of trays of the reactive distillation column, feeding point or points of the feed streams, the temperature of the cooler unit and/or reboiler, and the liquid residence time in the said column.

Preferably, the reactive distillation column comprises at least one column internal. Examples of such a column internal are a tray or packing. The number of trays of the reactive distillation column is also an important reaction parameter as these determine the effectiveness of the separation process of the reactants and products that takes place in the column, simultaneously with the reactions. Preferably, the number of trays in the column is at least 1, more preferably at least 2, and most preferably at least 5, and preferably at most 80, more preferably at most 60, most preferably at most 40. A skilled person further would understand that the size of the trays and the volume of the liquid, which each tray can contain, can vary and will also influence the reaction and/or separation effectiveness.

Desirably, the column will have trays, but any gas liquid contacting device might be suitable. Alternatively, suitable conventional packing, such as Raschig rings, Pall rings, saddles or structured packing of any kind might be used instead of trays. The different sections in the column might be equipped with different types of packing and/or trays.

The temperature of the cooler unit is lower than the reboiler temperature, and is chosen such that low-boiling products, such as the ethylene amine compound formed can leave the column, and that the reactants and high-boiling products remain in the system. The cooler unit can comprise just one cooler unit or may comprise a plurality of cooler sub-units, whereby each sub-unit has a specific temperature. A preferred embodiment of such a cooler unit comprises a first and a second cooler sub-unit. In a preferred embodiment a cooler unit is a condenser.

The person skilled in the art is capable of selecting the proper reactor and separation unit scheme by determining the overall yield, energy consumption and waste production.

The invention is illustrated by the below Examples.

Example 1

A batch distillation was performed by charging a distillation column with 0.301 mol of L-TETA, 0.287 mol DUTETA and 0.55 mol of U1TETA. The total moles of urea-groups in the system equalled 1.2 mol. The batch distillation column contained a packing of stainless steel wire mesh rings. A column length of 25 cm, corresponding to around 10 theoretical stages, was used during the experiments. Heat was supplied to the bottom section by an electrical heat plate with a metal jacket on top. The cooler in the top was cooled with cooling water with a temperature of around 10° C. A cold trap was placed between the cooler and the vacuum pump that was cooled with a mix of ethanol and dry ice. The distillation column was operated for 10 hours at pressures between 3 and 20 mbar, at temperatures between 200 and 250° C. The top fractions collected during distillation and the initial and final bottom fractions were analyzed using a GC-FID (gas chromatography using a flame ionization detector).

The GC-analysis data as given in below Table 1, shows that the amount of L-TETA that was recovered over the top of the distillation column, 0.41 mole, was larger than the amount of L-TETA that was added at the start of the experiment in the bottom of the column, 0.30 mole. The additional L-TETA obtained by partial conversion of U1TETA to L-TETA therefore accounts for an additional 0.11 mole L-TETA. The theoretical maximum L-TETA yield that could be obtained in this experiment was calculated to be 0.576 moles. The L-TETA yield in this experiment was therefore 70.8%.

TABLE 1

GC analysis of reactive separation of TETA mixture in Example 1

| | Start (mole) | End (mole) |
|---|---|---|
| L-TETA bottom | 0.301 | 0.072 |
| DUTETA bottom | 0.287 | |

TABLE 1-continued

GC analysis of reactive separation of TETA mixture in Example 1

|  | Start (mole) | End (mole) |
| --- | --- | --- |
| U1TETA bottom | 0.550 | |
| U in bottom | 1.2 | 1.2 |
| L-TETA top | | 0.408 |

Example 2

A water removal step was performed on a mixture containing 0.9 wt % L-TEPA, 19.2 wt % U1TEPA, 9.6 wt % U2TEPA, 48.5 wt % DU1TEPA, 11.9 wt % DU2TEPA and 12 wt % $H_2O$ by heating the reaction mixture to temperatures between 100-150° C. in a round bottom flask. After the water removal step, 100 grams of the remaining mixture containing 1.0 g, L-TEPA, 21.3 g U1TEPA, 10.7 g U2TEPA, 53.8 g DU1TEPA and 13.2 g DU2TEPA was transferred to a batch distillation column. The total moles of urea-groups in the system equalled 704 mmol. Table 2 gives the starting and end mixture of the water removal step in this Example 2.

TABLE 2

Analysis of composition in step to remove water from TEPA mixture

|  | Start (wt %) | Fraction after water removal (wt %) |
| --- | --- | --- |
| Composition of reaction mixture | | |
| L-TEPA | 0.9 | 1.0 |
| U1TEPA | 19.2 | 21.3 |
| U2TEPA | 9.6 | 10.7 |
| DU1,3TEPA | 48.5 | 53.8 |
| DU1,4TEPA | 11.9 | 13.2 |
| $H_2O$ | 12 | |
| Composition top | | |
| $H_2O$ | | 98% |
| Others | | 2% |

The composition obtained in the above water removal step was distilled. A batch distillation column containing a packing of stainless steel wire mesh rings with a column length of 25 cm, corresponding to around 10 theoretical stages, was used during the experiment. Heat was supplied to the bottom section by an electrical heat plate with a metal jacket on top. The cooler in the top was cooled with cooling water with a temperature of around 10° C. A cold trap was placed between the cooler and the vacuum pump that was cooled with a mix of ethanol and dry ice. The distillation column was operated for 10 hours at pressures between 3 and 17 mbar, at temperatures between 220 and 280° C. The top fractions collected during distillation and the initial and final bottom fractions were analyzed using a GC-FID (gas chromatography using a flame ionization detector).

The GC-analysis data shows that the amount of L-TEPA that was recovered over the top of the distillation column, 49 mmol, was larger than the amount of L-TEPA that was added at the start of the experiment in the bottom of the column, 5 mmol. The additional L-TEPA obtained by partial conversion of UTEPA to L-TEPA therefore accounts for an additional 44 mole L-TEPA. The theoretical maximum L-TEPA yield that could be obtained in this experiment was calculated to be 80 mmol. The L-TEPA yield in this experiment was therefore 62%.

The results of the reactive distillation are summarized in below Table 3

TABLE 3

GC analysis of reactive separation of TEPA mixture in Example 2

|  | Start of distillation (mmoles) | End of distillation (mmoles) |
| --- | --- | --- |
| Composition bottom | | |
| L-TEPA (bottom) | 5.3 | 0.7 |
| U1TEPA (bottom) | 99 | 4.9 |
| U2TEPA (bottom) | 49.5 | 7.4 |
| DU1,3TEPA (bottom) | 223 | 289 |
| DU1,4TEPA (bottom) | 54 | 80 |
| Composition top | | |
| L-TEPA (top) | | 49 |

This Example 2 not only shows the process of the invention for tetraethylene pentamine (TEPA) compositions but also that the process works with relatively high molar concentrations of urea derivatives.

The mixture obtained as bottom fraction at the end of the distillation in Example 2 was treated with a sodium hydroxide solution after which the amount of TEPA (i.e. tetraethylenepentamine without cyclic ethylene urea unit) on total (U)TEPA was increased.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process to convert a cyclic monourea of ethylene amine compounds into an ethylene amine compound, the process comprising:
performing a reactive separation step using a reaction mixture containing the cyclic monourea, wherein one cyclic monourea reacts with another cyclic monourea to transfer its urea unit thereto;
whereby the ethylene amine compound is separated from the reaction mixture.

2. The process of claim 1 wherein the ethylene amine compound is triethylene tetraamine or tetraethylene pentaamine.

3. The process of claim 2 wherein the ethyleneamine compound is triethylenetetraamine.

4. The process of claim 1 wherein the reaction is done in less than about 10 wt % of water on the basis of total weight of the reaction mixture.

5. The process of claim 1 wherein the reaction is done at a temperature of at least about 150° C.

6. The process of claim 1 wherein the reaction is done at a pressure of below about 1 bar.

7. The process of claim 1 further comprising hydrolyzing any urea compound DU-EA formed from reaction between at least two cyclic urea compounds with water, or water containing a base, to release its carbonyl group to provide carbon dioxide or an ionic derivative thereof.

8. The process further comprising separating of claim 7 the carbon dioxide or ionic derivative thereof.

9. The process of claim 1 further comprising recycling any urea compound DU-EA formed from reaction between at least two cyclic urea compounds back into the reactive separation process.

* * * * *